United States Patent
Lekholm et al.

[11] Patent Number: 5,699,788
[45] Date of Patent: Dec. 23, 1997

[54] ANAESTHETIC SYSTEM WHICH IS AUTOMATICALLY SWITCHED TO TEMPORARY OPERATION AS AN OPEN BREATHING SYSTEM UPON A CHANGE IN AN ANESTHETIC, AND METHOD FOR OPERATING SAME

[75] Inventors: Anders Lekholm, Bromma; Leif Wård, Dalarö, both of Sweden

[73] Assignee: Siemens Elema AB, Solna, Sweden

[21] Appl. No.: 645,501

[22] Filed: May 14, 1996

[30] Foreign Application Priority Data

Jun. 2, 1995 [SE] Sweden ................ 9502034

[51] Int. Cl.$^6$ .............. A61M 15/00; A61M 16/10; A62B 7/00; F16K 31/02
[52] U.S. Cl. .............. 128/203.12; 128/204.21; 128/205.24
[58] Field of Search .......... 128/203.12, 203.25–203.27, 128/204.21, 204.22, 205.23, 205.24, 202.22, 202.27

[56] References Cited

U.S. PATENT DOCUMENTS

| | | |
|---|---|---|
| 4,232,667 | 11/1980 | Chalon et al. .............. 128/911 |
| 4,281,652 | 8/1981 | Miller .............. 128/911 |
| 4,611,590 | 9/1986 | Ryschka et al. .............. 128/204.21 |
| 4,676,239 | 6/1987 | Humphrey .............. 128/911 |
| 4,791,922 | 12/1988 | Lindsay-Scott et al. . |
| 4,883,051 | 11/1989 | Westenskow et al. .............. 128/204.21 |
| 4,905,685 | 3/1990 | Olsson et al. .............. 128/204.21 |
| 4,989,597 | 2/1991 | Werner .............. 128/204.21 |
| 5,070,871 | 12/1991 | Manicom . |
| 5,245,996 | 9/1993 | Manicom . |
| 5,311,861 | 5/1994 | Miller .............. 128/912 |
| 5,520,168 | 5/1996 | Whitaker .............. 128/203.12 |

*Primary Examiner*—Kimberly L. Asher
*Attorney, Agent, or Firm*—Hill, Steadman & Simpson

[57] ABSTRACT

An anaesthetic system, which can be switched between an open system and a rebreathing system, includes a breathing circuit, a setting unit and a switching unit. When the breathing circuit is connected as a rebreathing system and a change in anaesthetic concentration or a change of anaesthetic type is initiated via the setting unit, the switching unit automatically sets the breathing circuit as an open system for a predetermined period of time, at the end of which the breathing circuit is automatically reset as a rebreathing system.

9 Claims, 1 Drawing Sheet

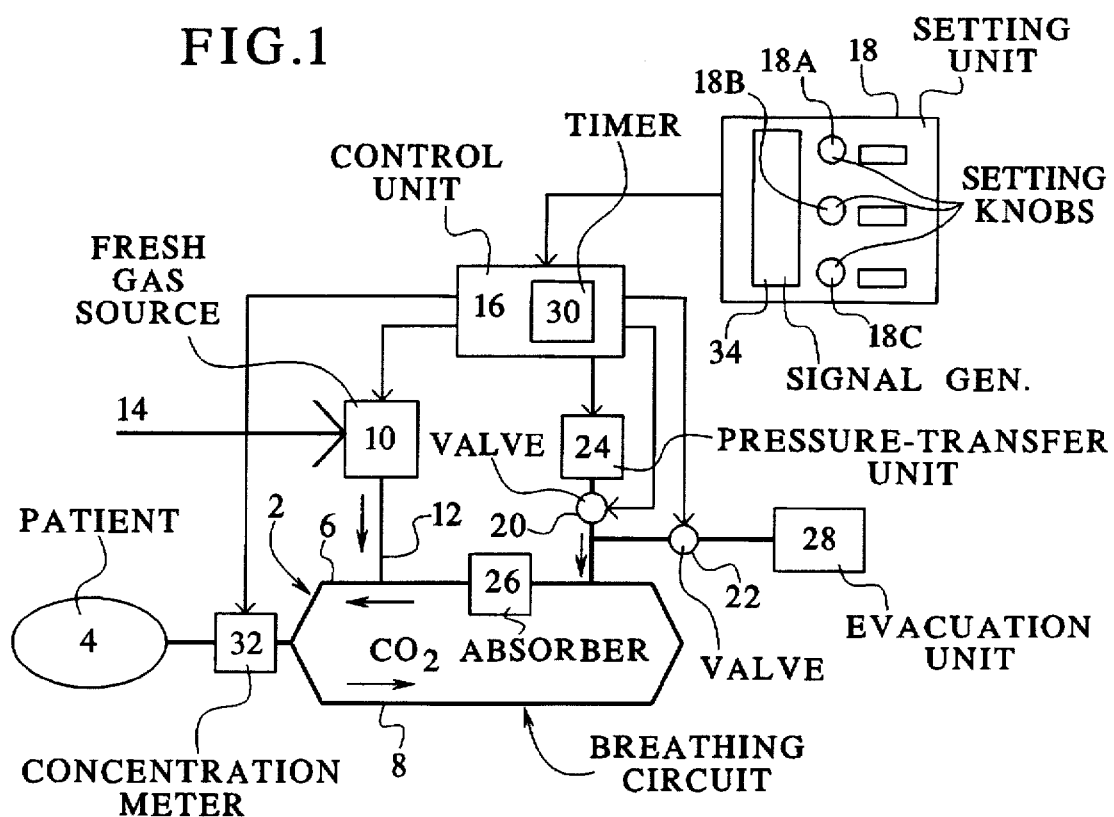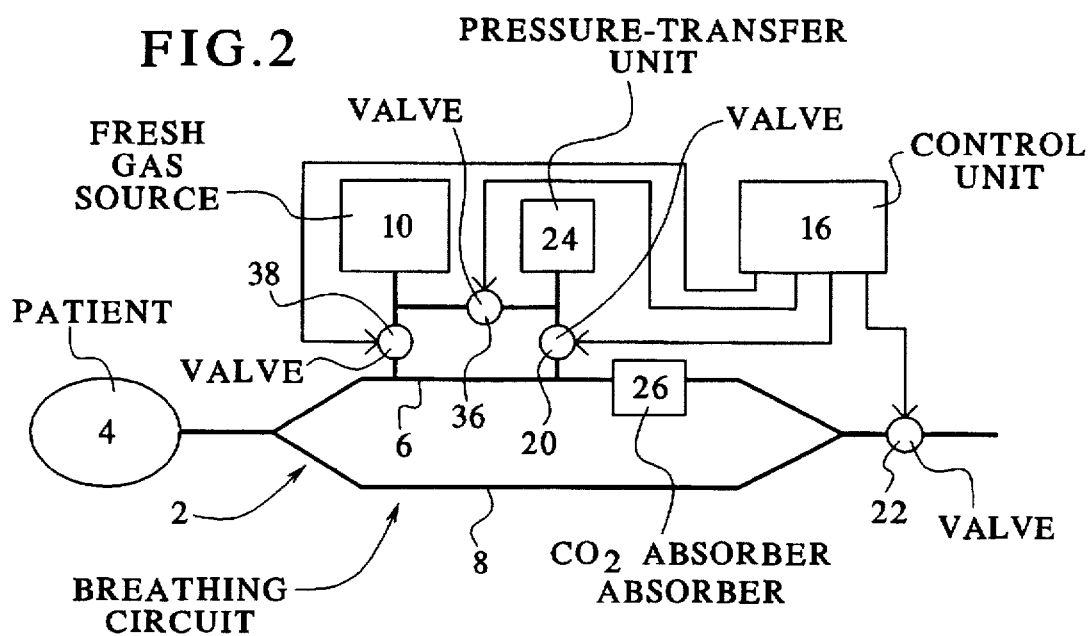

ANAESTHETIC SYSTEM WHICH IS AUTOMATICALLY SWITCHED TO TEMPORARY OPERATION AS AN OPEN BREATHING SYSTEM UPON A CHANGE IN AN ANESTHETIC, AND METHOD FOR OPERATING SAME

BACKGROUND OF THE INVENTION

1. Field of the Invention

The present invention relates to an anaesthetic administration system and to a method for administering anesthetic.

2. Description of the Prior Art

In the anaesthetic field, a large number of breathing systems for delivering gas to a patient are well-known. In the following description, only the abbreviated designation "system" will be used. In principle, these systems can be divided into two categories: open systems and rebreathing systems. In an open system, only fresh respiratory gas (containing oxygen, nitrous oxide, anaesthetic and, possibly, air in specific proportions) is supplied to the patient at each breath, and all expired respiratory gas is removed by an evacuation unit. In a rebreathing system, part of the expired respiratory gas is recirculated to the patient at the same time as supplementary fresh respiratory gas is added to the recirculated respiratory gas.

A number of different kinds of rebreathing systems exist in which a larger or smaller part of the expired respiratory gas is recirculated to the patient or in which only one or several of the gases in the exhaled respiratory gas is/are recirculated. In the most extreme rebreathing systems, virtually all expired respiratory gas is recirculated, with carbon dioxide being first removed from the expired respiratory gas. This kind of system is normally referred to as a closed system.

Anaesthetic equipment is therefore designed for operation with a number of different systems. One example of such anaesthetic equipment is described in U.S. Pat. No. 4,791, 922. The anaesthetic equipment disclosed therein includes a valve system which can be set to the system used. Setting can be performed without detaching or shifting gas tubes etc.

The respiratory gas supplied to the patient contains an anaesthetic gas. The five most common anaesthetic gases are halothane, enflurane, isoflurane, sevoflurane and desflurane. The effect of the different anaesthetic gases varies from patient to patient, and the gases cause different side-effects. An anesthesiologist thus may sometimes wish to switch to another anaesthetic during ongoing treatment. The anesthesiologist may induce narcosis with halothane and then switch to, e.g., sevoflurane. Patient allergy may be another reason to change the anaesthetic. Many anaesthetic administration systems therefore are equipped with a number of anaesthetic gas sources (usually in the form of vaporizers for liquid anaesthetic), and the physician or anesthesiologist can switch to another anaesthetic with a simple operation.

A problem arises, however, when anaesthetic is changed in rebreathing systems, especially when a larger part of the expired respiratory gas is recirculated to the patient. A mixture of different anaesthetic gases should not be given to the patient. This is because, inter alia, the effect of the mixture on the patient is unpredictable and can lead to complications. In addition, the concentration of anaesthetic in a mixture is unknown, or at least difficult to determine.

Another problem with rebreathing systems is that any change in the concentration of anaesthetic (even without any change in anaesthetic) occurs slowly in the breathing circuit. This is particularly apparent when the concentration is to be reduced in closed systems. A large part of the expired volume of respiratory gas, holding a higher concentration of anaesthetic gas than the desired concentration, is then recirculated to the patient.

SUMMARY OF THE INVENTION

An object of the present invention is to provide an anaesthetic system which solves the aforementioned problems.

Another object is to achieve a method for administering anaesthetic, which solves the aforementioned problems.

The above object is achieved in accordance with the principles of the present invention in an anesthetic system which can be switched between an open system and a rebreathing system. When the breathing circuit is connected as a rebreathing system and a change in anesthetic concentration and/or a change of anesthetic type is initiated via a setting unit, a switching unit automatically sets the breathing circuit as an open system for a predetermined period of time, at the end of which the breathing circuit is automatically reset as a rebreathing system.

As used herein the term "change in anesthetic" includes one or both of a change from one type of anesthetic to another type and a change in concentration of the anesthetic with the anesthetic type remaining the same.

When a switching unit is connected to a setting unit, the switching unit can be devised so that it automatically switches the breathing circuit whenever a change in the setting is initiated on the setting unit. In particular, the breathing circuit can be switched to an open system when the patient is to be given another anaesthetic or when the concentration of anaesthetic is to be reduced. The breathing circuit then remains set up as an open system for a predetermined period of time before the switching unit automatically switches the breathing circuit back to a rebreathing system.

DESCRIPTION OF THE DRAWINGS

FIG. 1 shows a first embodiment of an anaesthetic system.

FIG. 2 shows a breathing circuit in a second embodiment of an anaesthetic system constructed in accordance with the principles of the present invention.

DESCRIPTION OF THE PREFERRED EMBODIMENTS

FIG. 1 shows a schematic rendition of a first embodiment of the inventive anaesthetic system. Only functional blocks and components relevant to the invention are shown. The different functional blocks can each consist of a plurality of interconnected devices, and a plurality of functional blocks, or parts thereof, can be integrated into a single machine.

A breathing circuit 2 is connected to a patient 4 to supply the patient 4 with a respiratory gas. The respiratory gas consists of a predefined mixture of oxygen, nitrous oxide, anaesthetic gas and, possibly, air. The respiratory gas is carried to the patient 4 in an inspiratory line 6 and conveyed from the patient 4 in an expiratory line 8. Fresh respiratory gas can be delivered to the breathing circuit 2 from a fresh gas source 10 via a fresh gas line 12.

The fresh gas source 10 is supplied with component gases, such as oxygen and nitrous oxide, from external gas sources 14. The components are mixed in predefined proportions in the fresh gas source 10 and anaesthetic gas is added from vaporizers within the fresh gas source 10. The fresh gas source 10 can contain one vaporizer for every common anaesthetic or for a selection of anaesthetic (i.e. some or all of the anaesthetic halothane, desflurane, enflurane, isoflurane and sevoflurane). A predefined flow of respiratory gas is carried from the fresh gas source 10 to the breathing circuit 2, continuously or intermittently.

The breathing circuit 2 can operate according to a number of different systems, both as an open system and as type of any rebreathing system, in particular as a closed system. During ongoing usage, active system is selected by a switching unit having a control unit 16, a first valve 20 and a second valve 22.

The operator, usually an anaesthesiologist, initially selects the system to be used. This is performed by means of a setting unit 18 having a number of setting knobs 18A, 18B and 18C. The anesthesiologist can set all the parameters for the narcosis, i.e., the anaesthetic to be used, the concentration of the anaesthetic and the type of system other settings are the type of patient (e.g. child or adult), the volume to be delivered to the patient in each breath, the breathing rate to be used, etc.

Information corresponding to the parameters which have been set is sent from a signal generator 34 in the setting unit 18 to the control unit 16 as a control signal. The control unit 16 then regulates all functions necessary to the breathing circuit, e.g., the fresh gas source 10, the first valve 20 and the second valve 22.

If the breathing circuit 2 is to operate as an open system, the control unit 16 closes the first valve 20. Fresh respiratory gas is sent to the breathing circuit 2 at a relatively high flow rate, i.e. up to more than 10 liters a minute for an adult patient, when flow is continuous. The respiratory gas passes through the fresh gas line 12 to the inspiratory line 6 and on to the patient 4. During expiration, expired gas, with some fresh gas, passes through the expiratory line 8 out of the breathing circuit via the second valve 22 to an evacuation unit 28. Expensive anaesthetic gases can be recovered in the evacuation unit, and other gases can be released.

The second valve 22 can be a controllable valve, actively regulated by the control unit, a passive pressure relief valve which automatically opens at a specific excess pressure, e.g., 3 cm $H_2O$, or any combination thereof.

If the breathing circuit is to operate as a closed system, the first valve 20 opens while the second valve 22 is kept closed. The breathing circuit 2 fills with fresh respiratory gas from the fresh gas source 10, which thereafter only injects a very small amount of supplementary fresh gas to compensate for gas intake and oxidation in the patient, minor leakage etc. "Leakage" refers mainly to gas discharged through the second valve 22 in pressure peaks.

A pressure-transfer unit 24 applies rhythmic pressure changes to gas in the breathing circuit 2 and, accordingly, controls the patient's breathing. The pressure-transfer unit 24 can be a bag and bottle, well-known in the anesthesiology art.

During inspiration, gas from the pressure-transfer unit 24 is forced through the inspiratory line 6 and passes a carbon dioxide absorber 26. The carbon dioxide absorber 26 absorbs carbon dioxide in air expired by the patient 4. In expiration, the pressure-transfer unit 24 fills with gas from the expiratory line 8 and the patient 4 exhales. Expired gas is then returned to the patient 4 in the next inspiration.

One major advantage of the closed system is its low consumption of anaesthetic gas. Virtually all anaesthetic gas is immediately recirculated, breath after breath. The closed system is therefore preferred by many anesthesiologist.

Other rebreathing systems are also frequently employed, however, the degree of rebreathing can vary considerably in other rebreathing systems.

It is common for an anesthesiologist to wish to change the concentration of an anaesthetic or switch to another anaesthetic during ongoing treatment. This can cause problems, especially in the closed system. The inventive anaesthetic system has been devised in a special way to facilitate making changes in concentration and anaesthetic.

Assume that the patient 4 has been anaesthetized with halothane as the anaesthetic gas and the anesthesiologist then wishes to switch to sevoflurane. Sevoflurane is then selected on the setting unit instead of halothane. The desired concentration of sevoflurane is set at the same time.

The control unit 16 then controls the fresh gas source 10, causing a vaporizer for sevoflurane to be connected instead of one for halothane, and simultaneously activates a timer. The timer 30 then counts down for a predetermined period of time. During this time, the first valve 20 stays closed and the second valve 22 stays opens. In other words, the breathing circuit 2 is switched to an open system. Respiratory gas containing halothane in the breathing circuit 2 is then quickly flushed out through the evacuation unit. The lungs of the patient 4 are also emptied of respiratory gas containing halothane after a number of breaths. At the same time, relatively large amounts of respiratory gas containing sevoflurane are sent to the breathing circuit 2 from the fresh gas source 10 and fill the breathing circuit 2. When the predetermined period of time has elapsed, the first valve 20 re-opens, the second valve 22 closes and the flow of fresh gas from the fresh gas source 10 is reduced.

A rapid reduction in concentration can be achieved in a closed system in a corresponding manner.

The predetermined period of time can range from about 10 seconds to several minutes, but one to two minutes is typical. The time can be programmed into the timer or can be dependent on different parameters, such as the type of patient (child or adult), tidal volume (volume per breath), the type and concentration of anaesthetic gas, etc. The various parameters are sent to the control unit 16 as a control signal, and the counter 30 counts down for a period of time based on these parameters.

A concentration meter 32 for anaesthetic can be arranged in the breathing circuit 2. Since switching anaesthetic is a fast operation, the concentration meter 32 does not need to be capable of distinguishing between different anaesthetic. The concentration meter 32, however, may have to be reset for different anaesthetic. This resetting is appropriately performed by the control unit 16, however, resetting can be carried out via the setting unit 18 or in some other manner.

FIG. 2 shows a breathing circuit of a second embodiment of the inventive anaesthetic system. Elements which can be identical have retained the same designation number as in FIG. 1. The main difference between the first embodiment and the second embodiment is that the carbon dioxide absorber 26 is located upstream of the pressure-transfer unit 24, and that the fresh gas unit 10 can be selectively connected to the inspiration line 6 via a third valve 36 and the pressure-transfer unit 24, or connected directly to the inspiration line 6 via a fourth valve 38. Expired gas will now in the closed system be purified from carbon dioxide before returning to the pressure-transfer unit 24 and the supply of fresh gas will be made either via the third valve 36 in immediate connection to the filling or emptying of the pressure-transfer unit 24, or via the fourth valve 38.

When the situation described above occurs, i.e., that a change in anaesthetic is ordered, the pressure-transfer unit 24 is emptied, the second valve 22 opens and a small amount of new gas, containing the new selected anaesthetic, can fill the pressure-transfer unit 24 while the first valve 20 and third valve 36 are kept open for a short time period. Then the first valve 20 and the third valve 36 are closed and the fourth valve 38 is opened. A large amount of new fresh gas is now supplied from the fresh gas unit 10 to flush out the inspiration line 6 and expiration line 8 from the previously used anaesthetic. Since the second valve 22 will be open at least during expiration, a relatively high continuous flow of new fresh gas will also flow in the opposite direction in the inspiration line 6 and empty the absorber 26 as well as the inspiration line 6 from the old anaesthetic and fill the line with the new anaesthetic. During inspiration the second valve 22 can be controlled to force the patient 4 to inhale.

With the inventive system the patient 4 will receive the new anaesthetic practically immediately after the change has taken place and it is only the exchange of the old anaesthetic to the new anaesthetic in the lungs of the patient 4 that will determine the necessary length of time for the system to be connected as an open system.

It should be noted that the setting unit 18 does not necessarily have to be a separate part of the anaesthetic system. For example, each anaesthetic vaporizer is normally devised with a separate setting knob. The timer 30, or a large part of the control unit 16, can be incorporated into part of the setting unit 18. Switching itself can also be completely mechanical.

The principle of the invention can be described most simply by the method in which the breathing circuit is automatically switched from a rebreathing system to an open system for a predetermined period of time, when an anaesthetic gas is switched or the concentration of anaesthetic is changed, and the rebreathing system is reactivated when the predetermined period of time elapses.

The same principles can be used when a patient is not anesthetized, whereby a respiratory gas free from anaesthetic is supplied.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an anesthetic system comprising a breathing circuit, switching means for switching said breathing circuit between operation as an open system and operation as a rebreathing system, and setting means for setting a type of anesthetic and an anesthetic concentration, the improvement comprising:

said setting means being connected said switching means and said setting means comprising means, when said breathing circuit is being operated as a rebreathing system, for automatically causing said switching means to switch said breathing circuit for operation as an open system for a predetermined period of time when a change in anesthetic is initiated via said setting means, and for automatically causing said switching unit to switch said breathing circuit back to operation as a rebreathing system after the expiration of said predetermined period of time.

2. The improvement of claim 1 wherein said setting means comprises means for causing said switching means to operate said breathing circuit as an open system for a predetermined period of time in a range between five seconds and three minutes.

3. The improvement of claim 1 further comprising:

an anesthetic concentration meter, settable for respectively measuring different anesthetics, connected to said switching means, and wherein said switching means comprises means for automatically setting said concentration meter for measurement of a new anesthetic when a change in anesthetic is initiated via said setting means.

4. The improvement of claim 1 further comprising:

an anesthetic concentration meter, settable for respectively measuring different anesthetics, connected to said setting means, and wherein said setting means comprises means for automatically setting said concentration meter for measurement of a new anesthetic when a change in anesthetic is initiated via said setting means.

5. The improvement of claim 1 wherein said setting means comprise a signal generator for generating a control signal upon said change in anesthetic, and wherein said switching means comprise a timer, supplied with said control signal, said timer generating an activation signal for said predetermined period of time following receipt of said control signal for operating said breathing circuit as an open system for said predetermined period of time.

6. The improvement of claim 5 wherein said signal generator comprises means for emitting said control signal with information identifying a duration of said predetermined period of time contained in said control signal.

7. The improvement of claim 5 wherein said switching means comprises a valve connected for interaction with said breathing circuit to control a flow path of a respiratory gas in said breathing circuit for causing said respiratory gas to selectively flow either in an open system or in a rebreathing system, said valve being connected to said timer and receiving said activation signal therefrom and causing said respiratory gas to flow in said breathing circuit as an open system as long as said activation signal is present.

8. A method for operating an anesthetic system having a breathing circuit comprising the steps of:

providing an anesthetic system comprising a breathing circuit and switching means;

operating said breathing circuit as a closed system and administering anesthetic, via said breathing circuit, to a patient connected to said breathing circuit;

initiating a change in anesthetic;

upon said change in anesthetic, said switching means automatically switching said breathing circuit for operation as an open system for a predetermined period of time; and after expiration of said predetermined period of time, said switching means automatically resetting said breathing circuit for operation as a closed system.

9. A method as claimed in claim 8 wherein said anesthetic system includes an anesthetic concentration meter, settable for respective measurement of a plurality of different anesthetics, and comprising the additional step of:

upon a change in anesthetic, automatically switching said anesthetic concentration meter for measurement of a new anesthetic.

* * * * *